US009238056B2

(12) United States Patent
Knudsen et al.

(10) Patent No.: US 9,238,056 B2
(45) Date of Patent: Jan. 19, 2016

(54) CYCLIC PEPTIDE AND CONJUGATE THEREOF FOR BINDING TO KERATINOCYTES

(75) Inventors: Nina Østergaard Knudsen, Ballerup (DK); Thorsten Thormann, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 8 days.

(21) Appl. No.: 14/000,811

(22) PCT Filed: Feb. 21, 2012

(86) PCT No.: PCT/EP2012/052955
§ 371 (c)(1),
(2), (4) Date: Sep. 20, 2013

(87) PCT Pub. No.: WO2012/113803
PCT Pub. Date: Aug. 30, 2012

(65) Prior Publication Data
US 2014/0023700 A1 Jan. 23, 2014

Related U.S. Application Data

(60) Provisional application No. 61/445,269, filed on Feb. 22, 2011.

(51) Int. Cl.
| | | |
|---|---|---|
| A61K 38/04 | (2006.01) | |
| A61K 31/593 | (2006.01) | |
| A61K 8/64 | (2006.01) | |
| A61K 38/12 | (2006.01) | |
| A61K 47/48 | (2006.01) | |
| C07K 7/06 | (2006.01) | |
| C07K 7/64 | (2006.01) | |
| A61K 9/127 | (2006.01) | |
| A61K 31/047 | (2006.01) | |
| A61K 38/00 | (2006.01) | |

(52) U.S. Cl.
CPC . *A61K 38/12* (2013.01); *A61K 8/64* (2013.01); *A61K 9/1271* (2013.01); *A61K 31/047* (2013.01); *A61K 47/48246* (2013.01); *A61K 47/48815* (2013.01); *C07K 7/06* (2013.01); *C07K 7/64* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,536,814 A | 7/1996 | Ruoslahti et al. | |
| 5,627,263 A | 5/1997 | Ruoslahti et al. | |
| 5,817,750 A | 10/1998 | Ruoslahti et al. | |
| 5,834,016 A * | 11/1998 | Naeff et al. | 424/450 |
| 5,955,572 A | 9/1999 | Ruoslahti et al. | |

FOREIGN PATENT DOCUMENTS

| | | | | |
|---|---|---|---|---|
| WO | WO 99/02551 A1 | 1/1999 | | |
| WO | WO99/02551 A1 * | 1/1999 | .............. | C07K 7/64 |
| WO | WO2009/052449 * | 4/2009 | .............. | C07K 7/04 |
| WO | WO 2009/052449 A1 | 4/2009 | | |

OTHER PUBLICATIONS

Michael Brinkley, A Brief Survey of Methods for Preparing Protein Conjugates with Dyes, Haptens, and Cross-Linking Reagents, Bioconjugate Chem, 1992, 3, 2-13.*
Koning et al., Antiproliferative effect of immunoliposomes containing 5-Fluorodeoxyuridine-dipalmitate on colon cancer cells, Br. Ji. Cancer, 1999, 80(11), 1718-1725.*
Schiffeler et al., Anti-tumor efficacy of tumor vasculature-targeted liposomal doxorubicin, Ji. Controlled Release, 91 (2003) 115-122.*
Korver et al., A double-blind, randomized quantitative comparison of calcitriol ointment and calcipotriol ointment on epidermal cell populations, proliferation and differentiation, Br. Ji. Derm., 2007 156, 130-137.*
Teige, Induced keratinocyte hyper-proflieration in a2B1 integrin transgenic mice results in systemic immune cell activation, Int. Immunopharm. 10 (2010) 107-114 (supplied in IDS).*
Boisvert et al., Alpha2beta1 integrin is the major collagen-binding integrin expressed on human Th17 cells, Eur. J. Immunol. 2010 40:2710-2719.*
Andrew et al., A quantitative immunohistological study of the expression of integrins by nerves in psoriatic and normal skin, Br. J. Derm. (1992) 127, 359-364.*
Conrad et al., α1β1 integrin is crucial for accumulation of epidermal T cells and the development of psoriasis, Nature Medicine, vo. 13, No. 7, Jul. 2007, pp. 836-842.*
Barczyk et al., "Integrins", Cell Tissue Res, 339, 2010, pp. 269-280.
Carroll et al., "Suprabasal Integrin Expression in the Epidermis of Transgenic Mice Results in Developmental Defects and a Phenotype Resembling Psoriasis" Cell, vol. 83, Dec. 15, 1995, pp. 957-968.
Emsley et al., "Structural Basis of Collagen Recognition by Integrin α2B1", Cell, vol. 101, Mar. 31, 2000, pp. 47-56.
International Search Report for PCT/EP2012/052955 dated Jul. 26, 2012.
Ivaska et al., "A Peptide Inhibiting the Collagen Binding Function of Integrin α2I Domain", The Journal of Biological Chemistry, vol. 274, No. 6, Feb. 5, 1999, pp. 3513-3521.
Knight et al., "The Collagen-binding A-domains of Integrins α1B1 and α2B1 Recognize the Same Specific Amino Acid Sequence, GFOGER, in Native (Triple-helical) Collagens" The Journal of Biological Chemistry, vol. 275, No. 1, Jan. 7, 2000, pp. 35-40.
Koning et al., "Targeting of Angiogenic Endothelial Cells at Sites of Inflammation by Dexamethasone Phosphate-Containing RGD Peptide Liposomes Inhibits Experimental Arthritis", Arthritis & Rheumatism, vol. 54, No. 4, Apr. 2006, pp. 1198-1208.
Lambert et al., "Competitive Interactions of Collagen and a Jararhagin-derived Disintegrin Peptide with the Integrin α2-1 Domain" The Journal of Biological Chemistry, vol. 283, No. 24, Jun. 13, 2008, pp. 16665-16672.

(Continued)

*Primary Examiner* — Karlheinz R Skowronek
*Assistant Examiner* — Joseph Fischer
(74) *Attorney, Agent, or Firm* — Birch Stewart Kolasch & Birch, LLP

(57) ABSTRACT

A cyclic peptide capable of binding specifically to the α2 I domain of a collagen binding integrin receptor may be conjugated to a drug containing particle via a linker moiety. The conjugate may be used to target a therapeutic drug to a cell expressing a collagen binding integrin receptor on its surface.

12 Claims, 4 Drawing Sheets

(56) References Cited

OTHER PUBLICATIONS

Manjappa et al., "Antibody derivatization and conjugation strategies: Application in preparation of stealth immunoliposome to target chemotherapeutics to tumor", Journal of Controlled Release, 150, 2011, pp. 2-22.

Mulder et al., "Molecular Imaging of Macrophages in Atherosclerotic Plaques Using Bimodal PEG-micelles", Magnetic Resonance in Medicine, 58, 2007, pp. 1164-1170.

Pentikäinen et al., ""RKKH" Peptides from the Snake Venom Metalloproteinase of Bothrops jararaca Bind Near the Metal Ion-dependent Adhesion Site of the Human Integrin α2 I-domain", The Journal of Biological Chemistry, vol. 274, No. 44, pp. 31493-31505.

Teige et al., "Induced keratinocyte hyper-proliferation in α2B1 integrin transgenic mice results in systemic immune cell activation", International Immunopharmacology, 10, 2010, pp. 107-114.

Watt, "Role of integrins in regulating epidermal adhesion, growth and differentiation" The EMBO Journal, vol. 21, No. 15, 2002, pp. 3919-3926.

Written Opinion of the International Searching Authority for PCT/EP2012/052955 dated Jul. 26, 2012.

Xiong et al., "Intracellular Delivery of Doxorubicin with RGD-Modified Sterically Stabilized Liposomes for an Improved Antitumor Efficacy: In Vitro and in Vivo", Journal of Pharmaceutical Sciences, vol. 94, No. 8, Aug. 2005, pp. 1782-1793.

Zaitsu et al., "Heme-Undecapeptide Labeling on Insulin for the Immunoassay of Insulin with Chemiluminescence Detection", Analytical Sciences, Sep. 1999, vol. 15, pp. 871-878.

\* cited by examiner

CYCLIC PEPTIDE AND CONJUGATE THEREOF FOR BINDING TO KERATINOCYTES

CROSS REFERENCE TO RELATED APPLICATIONS

This application is the National Phase of PCT/EP2012/052955 filed on Feb. 21, 2012, which claims priority under 35 U.S.C. 119(e) to U.S. Provisional Application No. 61/445,269 filed on Feb. 22, 2011, all of which are hereby expressly incorporated by reference into the present application.

FIELD OF INVENTION

The present invention relates to a cyclic peptide and conjugates thereof with drug-containing carrier particles for targeting drugs to keratinocytes by binding to a collagen binding integrin receptor on keratinocytes. The invention further relates to a pharmaceutical composition comprising said conjugate.

BACKGROUND OF THE INVENTION

The integrins are a family of integral membrane receptors which mediate cell-cell and cell-extracellular matrix interaction by regulating cell adhesion, differentiation, migration and the immune response. The integrins are heterodimers composed of $\alpha$ and $\beta$ subunits. Different combinations of subunits are expressed by different cell types generating a family of 25 different heterodimers. Some integrin receptors from the RGD binding subgroup, such as the $\alpha5\beta1$ and the $\alpha v \beta3$ integrin receptors, recognize the arginine-glycine-aspartic acid (RGD) motif in extracellular matrix proteins such as fibronectin. Peptides comprising the RGD motif or structural mimics thereof have been prepared and proposed as therapeutic entities binding to integrins, primarily the $\alpha5\beta1$ and the $\alpha v \beta3$ integrin receptor, thereby inhibiting the integrin-mediated cell attachment to extracellular matrix proteins such as fibronectin (cf. U.S. Pat. No. 5,536,814; U.S. Pat. No. 5,627,263; U.S. Pat. No. 5,817,750; U.S. Pat. No. 5,955,572). These peptides are proposed for use in wound healing and to prevent tumour cells from binding to fibronectin, thereby inhibiting metastasis. By binding integrin receptors expressed on proliferating endothelial cells, these peptides can improve the drug delivery during cancer progression and inflammation (G. A. Konning et al., Arthritis Rheum 54 (4) 2006 pp 1198-1208 and X. B. Xiong et al., J Pharm Sci 94 (8) 2005, pp 1782-1793).

The integrin $\alpha2\beta1$ receptor belongs to the integrin subgroup of collagen binding receptors. It binds several naturally occurring ligands such as collagen I, through the extracellular I domain of the integrin $\alpha2$ monomer (the a$\alpha2$ I domain), which is conserved in all collagen binding integrin receptors (M. Barczyk et al., Cell tissue Res 339 (1) 2010 pp 269-280). The interaction occurs in a cation-dependent manner, the interaction between collagen I and the integrin $\alpha2\beta1$ receptor being mediated via $Mg^{2+}$-bridged interactions supported by the MIDAS motif residues (Asp 151, Ser 153, Thr 221 and Asp 254) (L. J. Lambert et al., J. Biol. Chem. 283 (24), 2008, pp. 16665-16672). Solving the structure of the integrin $\alpha2$ domain in complex with a collagen triple helix of three 21 amino acid collagen-derived peptides revealed that the $\alpha2$ I domain undergoes conformational changes upon interaction with collagen (Emsley et al., Cell. 101 (1), 2000, pp 47-56). Such conformational changes in the receptor on interaction with the collagen peptide were confirmed by NMR spectroscopy (Lambert, supra). The presence of the triplex peptide also inhibits interaction between the integrin $\alpha2$ and full-length collagen (Knight et. al., J. Biol. Chem. 275 (1), 2000, pp 35-40).

Binding of collagen and fibrinogen-dependent platelet activity may be inhibited by polypeptide toxins derived from snake venom, contributing to the anticoagulant effect of these venoms. These polypeptides (termed disintegrins) are functional homologues of the RGD motif found in extracellular matrix proteins. The jararhagin protein isolated from the venom of *Bothrops jararaca* (the Brazilian pit viper) has been found to inhibit collagen I interaction (J. Ivaska et al., J. Biol. Chem. 274 (6), 1999, pp. 3513-3521). A basic motif, Arg-Lys-Lys (RKK), in jararhagin is important for the interaction. A nine amino acid long cyclic peptide ($C^{241}$TRKKHDNAQ$^{249}$C)(SEQ ID NO: 3) has been found to inhibit the interaction between collagen I and the integrin $\alpha2\beta1$ receptor in the presence of 2 mM MgCl2 (Ivaska et al., supra) by binding competitively to $\alpha2$ I domain and disrupting cell adhesion to collagen I.

The nine amino acid peptide containing the RKK motif disclosed by Ivaska et al., supra, and other cyclic peptides containing the RKK motif derived from jararhagin are disclosed in WO 99/02551 and proposed for use in therapy to block integrin interaction with collagen and laminin, more specifically to block cell migration on collagen, e.g. as seen in periodontitis, or to block migration of malignant cells, e.g. as seen in osteosarcoma or malignant melanoma, or to prevent platelet adhesion to collagen, e.g. as seen in thrombosis and stroke. The peptides disclosed in WO 99/02551 preferably contain a cysteine residue at both ends such that the peptide may be cyclized by disulfide bond formation between the two cysteines.

The integrin $\alpha2\beta1$ receptor has been found to be expressed in high amounts in skin keratinocytes (F. Watt, EMBO J., 21 (15), 2002, pp 3919-3926). In normal skin, the receptor is confined to the proliferating basal layers of the epidermis, but during wound healing and in psoriasis, the receptor is expressed on keratinocytes in the suprabasal layers correlating with an altered keratinocyte differentiation. Transgenic mice expressing the integrin $\alpha2\beta1$ receptor under the involucrine promoter have previously been demonstrated to spontaneously develop a skin disorder resembling psoriasis (J. M. Carroll et al., *Cell* 83, 1995, pp. 957-968). It has furthermore been shown that in integrin transgenic mice a mild epidermal wounding leads to chronic inflammation similar to the Koebner phenomenon in psoriasis patients in whom wounding of non-lesional skin often results in the development of a psoriatic plaque at the site of the wound. The mice were followed for five weeks and throughout that time exhibited substantial keratinocyte hyperproliferation, inflammatory infiltration and high cytokine levels within the skin. Furthermore, the systemic immune response was very much affected with increased spleen size, elevated cytokine levels in serum and altered lymphocyte trafficking resembling what is seen in psoriasis patients (I. Teige et al., *Int. Immunopharmacol.* 10, 2010, pp. 107-114).

It is an object of the invention to provide a dermal drug delivery system utilizing integrin receptors expressed on keratinocytes in the lower epidermis as well as on inflammatory cells present in skin to target pharmacologically active compounds to this specific layer of the skin with a view to treating dermal diseases located in the lower epidermis (e.g. psoriasis, wounds, skin cancer and atopic dermatitis).

SUMMARY OF THE INVENTION

Accordingly, in one aspect the invention relates to a cyclic peptide capable of binding specifically to the $\alpha2$ I domain of an integrin receptor of the subgroup of collagen binding integrin receptors said peptide having the amino acid sequence $$X_1-X_2-X_3-X_4-X_5-X_6-X_7-X_8-X_9-X_{10}-X_{11}-Lys-L \quad \text{(SEQ ID NO: 1)}$$

wherein
$X_1$ is an amino acid residue selected from the group consisting of Ser, Thr, Leu and Ile;
$X_2$ is an amino acid residue selected from the group consisting of Thr and Ser;
$X_3$ is an amino acid residue selected from the group consisting of Arg;
$X_4$ is an amino acid residue selected from the group consisting of Lys;
$X_5$ is an amino acid residue selected from the group consisting of Lys;
$X_6$ is an amino acid residue selected from the group consisting of His and Lys;
$X_7$ is an amino acid residue selected from the group consisting of Asp, Glu, Ala, Asn and Gln;
$X_8$ is an amino acid residue selected from the group consisting of Gln, Asn, Ala, Glu and Asp;
$X_9$ is an amino acid residue selected from the group consisting of Ala, Gly, Val, Leu and Ile;
$X_{10}$ is an amino acid residue selected from the group consisting of Gln, Asn, Glu and Asp; X11 is
an amino acid residue selected from the group consisting of Ser and Thr;
and
L is a linker moiety suitable for conjugating a drug-containing carrier particle, the linker moiety comprising a thiol group; and a pharmaceutically acceptable carrier or excipient.

It is envisaged that each of the amino acid residues proposed for positions $X_1$-$X_{11}$ may be replaced with an amino acid analogue mimicking the structural and/or physicochemical features (e.g. charge) of the amino acid indicated above to be suitable for use in each of these positions.

In another aspect, the invention relates to a drug conjugate comprising said cyclic peptide and a drug-containing carrier particle conjugated to the linker moiety L.

In a further aspect, the invention relates to the use of said conjugate for targeting a therapeutic drug contained in the carrier particle to a cell expressing the integrin $\alpha 2\beta 1$ receptor on its surface.

In a still further aspect, the invention relates to the use of said conjugate in the treatment of dermal diseases or conditions (in the epidermis).

While conjugates of a cyclic RGD peptide and a drug-containing liposome have been investigated for targeting of drug loaded particles such as liposomes to the integrin αv receptor with a view to treating cancer by systemic administration (R. Schiffeler, et al., Int. J. Pharm. 364, 2008, pp 258-264), it is believed to be novel to utilize a cyclic peptide of the present invention to target a drug-containing carrier particle such as a liposome to a collagen binding integrin receptor such as the integrin $\alpha 2\beta 1$ receptor expressed on keratinocytes by topical administration with a view to treating dermal diseases. The peptides disclosed by Ivaska et al., supra, and in WO 99/02551 include a cysteine residue at both ends and are cyclized by the formation of a disulfide bond between the two cysteines. This makes them unsuitable for conjugating to liposomes or other carrier particles as the linker(s) since thiol groups are often used for the conjugation (e.g. SATA). Free thiol groups might interact with the disulfide bond so as to generate polymeric peptides rather than conjugates with the carrier particles, or the linker may possibly cyclize with one of the cysteines. Thus, under reducing conditions, the disulfide bond may open to form a linear peptide or cause peptide oligomerization or both. Furthermore, a peptidic linker joins the N- and the C-terminal of the backbone of the new peptides, which in general decreases their susceptibility to enzymatic degradation in biological tissues (Lovelace et al., 2006 J. Med. Chem. 49, 6561-6568). The cyclic conformation of the peptide is important for its interaction with the integrin receptor (Ivaska et al., supra), and the stability of the cyclic peptide may therefore be important in an in vivo environment.

DETAILED DESCRIPTION OF THE INVENTION

Definitions

Figure 1:
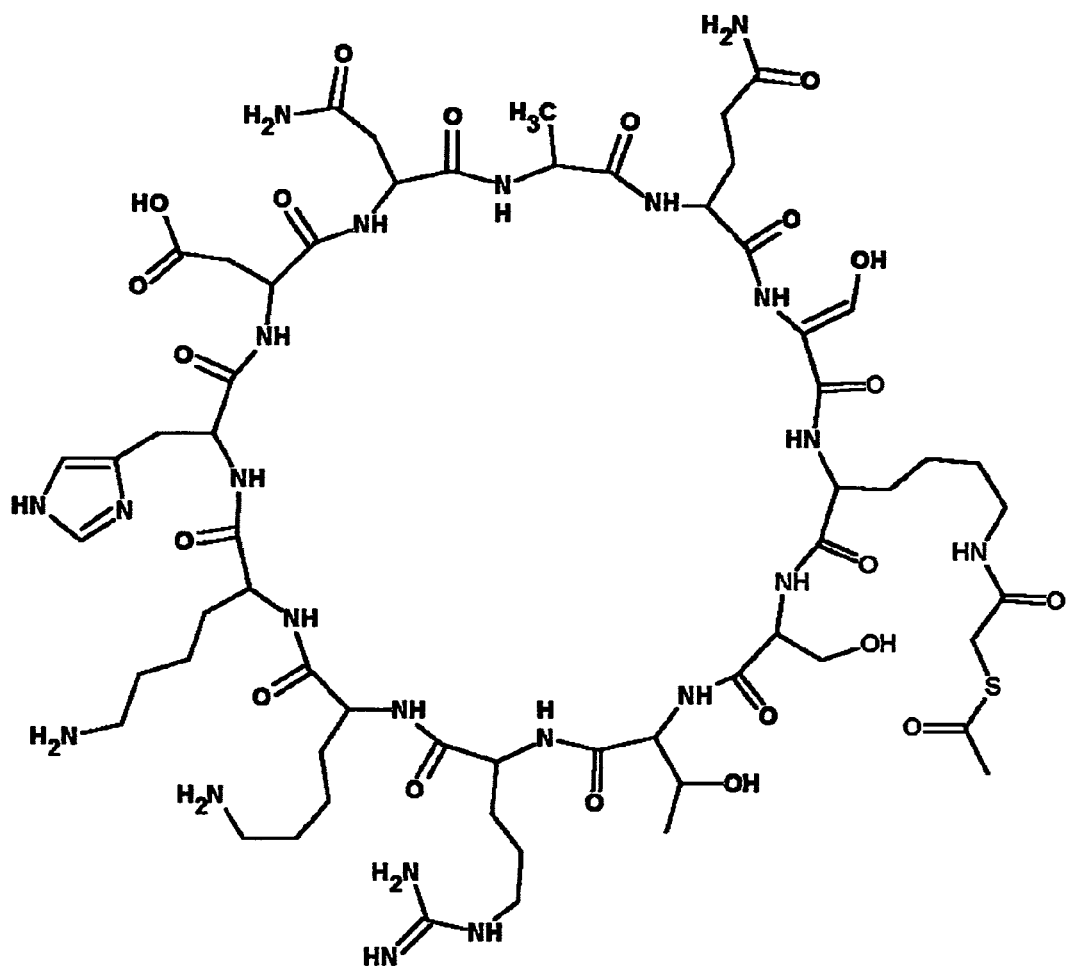
FIG. 1 shows the chemical structure of an embodiment of the peptide of the invention.
Figure 2:
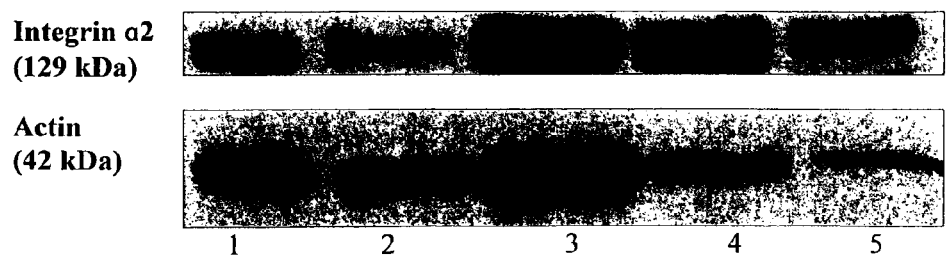
FIG. 2 is a Western blot showing the expression of the integrin $\alpha 2\beta 1$ receptor in different cell types: (1) in a skin biopsy from the transgenic mouse model which is homozygous for the human integrin $\alpha 2\beta 1$ receptor, (2) in a cell extract from A431 cells (an human epidermal carcinoma cell line), (3) primary human keratinocytes isolated tissues removed by human breast reduction, and (4) and (5) two human human keratinocyte cell lines ((4) HaCat and (5) Kert) used at LEO Pharma.

In the present context, the term "peptide" is intended to indicate a compound comprising a sequence of amino acid residues connected by peptide bonds formed by reaction between adjacent carboxyl and amino groups.

The term "integrin receptor" is intended to indicate a receptor that belongs to the subgroup of collagen binding integrin receptor that all include the extracellular I domain of the integrin α2 monomer (the α2 I domain), including the integrin $\alpha1\beta1$, $\alpha2\beta1$, $\alpha10\beta1$ and $\alpha11\beta1$ receptors.

The term "amino acid" is intended to indicate a naturally occurring amino acid (or amino acid residue) or non-naturally occurring amino acid analogue. Example of naturally occurring amino acids are L-amino acids and D-amino acids selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine and citrulline. Examples of non-naturally occurring amino acids include synthetic compounds mimicking the structural and/or physicochemical features (e.g. charge) of a naturally occurring amino acid, e.g. compounds that include a carboxyl group and an amino group attached to an α-carbon atom, but with modifications or substitutions of the side chain.

The term "binding specifically" or "specific binding" is intended to indicate the ability of the peptide of the invention to bind to the α2 I domain of collagen binding integrin receptors such as the α2β1 receptor in a similar manner as the RKK peptide disclosed by Ivaska et al., supra. By way of comparison, a peptide which has a similar amino acid composition and charge as the peptide of the invention, but which does not include the RKK motif, does not bind specifically to the α2 I domain of collagen binding integrin receptors.

The term "liposome" is intended to indicate spherical lipid vesicles with a bilayer structure which exhibit favourable properties in terms of drug penetration enhancement into the skin, improved pharmacological effects, increased stability of the drug, decreased side effects and controlled drug release compared to non-vesicular drug delivery systems. The drug penetration properties may depend on preparation methods, lipid composition means sizes and the physicochemical properties of the drugs included in the liposomes.

The term "niosome" is intended to indicate vesicles formed from non-ionic amphiphilic surfactants in aqueous media. Niosomes exhibit a bilayer structure similar to that of liposomes.

The term "transfersome" is intended to indicate ultradeformable vesicles composed of phospholipids and a single chain surfactant to destabilize the lipid bilayer of the vesicles and increase the deformability of the bilayer by lowering its interfacial tension.

The term "polymeric nanoparticle" is intended to indicate particles of a size of less than 1 μm forming a porous or dense polymeric matrix in which a drug substance is adsorbed or entrapped, or nanocapsules in which a drug-containing core is enclosed by a shell of a polymeric material.

The term "lipid nanoparticle" is intended to indicate a solid lipid nanoparticle (SLN) or nanostructured lipid carrier (NLC). Solid lipid nanoparticles are composed of solid lipids and surfactants and have a mean particle diameter of 50-1000 nm. Nanostructured lipid carriers are composed of mixtures of solid lipids and liquid lipids (oils) and surfactants. While the NLCs are solid at room temperature, they have a lower melting point than SLNs. Both types of lipid nanoparticles comprise a therapeutically active ingredient as a solid solution or dispersion in the lipid material.

Embodiments

In an embodiment of the cyclic peptide of the invention $X_1$ is Ser.

In an embodiment of the cyclic peptide of the invention, $X_2$ is Thr.

In an embodiment of the cyclic peptide of the invention, $X_3$ is Arg.

In an embodiment of the cyclic peptide of the invention, $X_4$ is Lys.

In an embodiment of the cyclic peptide of the invention, $X_5$ is Lys.

In an embodiment of the cyclic peptide of the invention, $X_6$ is His.

In an embodiment of the cyclic peptide of the invention, $X_7$ is Asp.

In an embodiment of the cyclic peptide of the invention, $X_8$ is Asn.

In an embodiment of the cyclic peptide of the invention, $X_9$ is Ala.

In an embodiment of the cyclic peptide of the invention, $X_{10}$ is Gln.

In an embodiment of the cyclic peptide of the invention, $X_{11}$ is Ser.

In a currently preferred embodiment, the cyclic peptide of the invention has the amino acid sequence

```
                                           (SEQ ID NO: 2)
Ser-Thr-Arg-Lys-Lys-His-Asp-Asn-Ala-Gln-Ser-Lys-L
``` wherein L is as defined above.

In the cyclic peptide of the invention, the linker moiety L may include any SH group that may interact with the mal-PEG-liposome. The L moiety may comprise other groups if the liposomal conjugation is mediated by another group than maleimide-PEG, cf. Table 1 of L. Nobs et al., *J. Pharm. Sci.* 93, 2004, pp. 1980-1992.

The liposome may contain a group for conjugation of the ligand. The active group for conjugation can be Amino-PEG-DSPE, carbodiimide mediated coupling, hydrazine-PEG-DSPE, HS-PEG-distearoyl phosphoethanolamine (DSPE), Maleimide-PEG or nitrophenyl carbonate. Examples of suitable linker moieties L are S-succinimidyl-5-thioacetate (SATA), N-hydroxysuccinimidyl 3-(2-pyridyldithio) propionate (SPDP), N-succinimidyl N-acetyl-thiopropionate (SATP), succinimidyl S-acetyl(thiotetraethylene glycol) (SAT-PEO$_4$-Ac), carbodiimide (e.g. 1-ethyl-3-(3-dimethylaminopropyl)carbodiimide). When the linker moiety L is SATA, conjugation of the peptide to the drug carrier particles may conveniently be carried out by activation of the thiol group of the linker and reaction with maleimide groups on the surface of the carrier particle (R. Schiffeler et al., J. Control. Release 91, 2003, pp 115-122). As previously indicated, while SATA is a convenient linker moiety for that reason, it is not suitable to use this linker with the cyclic peptides disclosed by Ivaska et al., supra, which are cyclized by disulfide bond formation between two cysteine residues at either end of the peptide as the activated thiol group of the linker might interact with the disulfide bond or generate polymeric peptides rather than conjugates with the carrier particles, or the linker may possibly cyclize with one of the cysteines.

The present peptides may conveniently be prepared by chemical synthesis, such as by solid phase peptide synthesis (Merrifield, et al., *J. Am. Chem. Soc.* 85, 1964, p. 2149) assembling the linear peptide chain using Fmoc protected amino acids. The peptide may be cyclized after release from the resin by forming an amide bond between the terminal Lys and the amino acid at the other terminal.

The present peptide is preferably one that binds specifically to the integrin α2β1 receptor expressed on keratinocytes in the lower epidermis thus enabling targeting of the drug-containing carrier particle to the keratinocytes where the drug may exert its activity. The drug-containing carrier particle conjugated to the present cyclic peptide may conveniently be a liposome, niosome, transfersome, polymeric nanoparticle or lipid nanoparticle.

When the carrier particle is a liposome, it may conveniently comprise one or more of the lipids phosphatidylcholine, phosphatidylethanolamine, phosphatidic acid, phosphatidylglycerol, phosphatidylserine, phosphatidylinositol, dioleoyl trimethylammonium propane (DOTAP) or dioleyloxypropyl trimethylammonium (DOTMA). It may also comprise a steroid (e.g. cholesterol) or a surfactant (e.g. cholate, sorbitan esters, or polysorban esters). Liposomes may be prepared by dry lipid film hydration, emulsification, reverse phase evaporation, freeze-thaw processes or solvent injection. Size homogenization may be prepared by extrusion or sonication.

The ligand may be conjugated to the surface of liposomes in two ways, either by conjugation of the ligand to a hydrophobic anchor before preparation of the liposome or by coupling of the ligand to the surface of a liposome after preparation, cf. Nobs et al., supra.

It may be particularly advantageous that at least one lipid included in the liposomes comprises PEG groups and maleimide attached thereto. Maleimide groups attached to the liposomes are convenient for conjugating the liposomes to a linker containing thiol groups such as SATA. PEG groups form a convenient linker between the liposome and the maleimide group.

When the carrier particle is a niosome, it may conveniently comprise one or more non-ionic surfactants selected from the group consisting of polyethylene glycol alkyl ethers (e.g. polyoxyethylene-2-stearyl ether or polyoxyethylene-10-oleyl ether), sorbitan esters (e.g. sorbitan palmitate, sorbitan laurate, sorbitan stearate, sorbitan tristearate or sorbitan oleate), sucrose laurate ester, polysorbate or cholesterol. Niosomes may be prepared by a process including dry lipid film hydration, emulsification, reverse phase evaporation, freeze-thaw processes or solvent injection. Size homogenization may be prepared by extrution or sonication.

When the carrier particle is a polymeric nanoparticle, it may comprise one or more of polylactic acid, polyglycolic acid, poly(lactic-co-glycolic acid), polycaprolactone, polyvinyl acetate, polyalkylcyanoacrylates), polystyrene, polydimethylsiloxane or chitosan. Polymeric nanoparticles may be prepared by a procedure including dispersion of preformed polymers or by in situ polymerization techniques.

When the carrier particle is a solid lipid nanoparticle or a nanostructured lipid carrier, it may comprise one or more solid lipids, e.g. triglycerides, partial glycerides, fatty alcohols, steroids or waxes, as well as emulsifiers, such as poloxamer 188, polysorban esters, polyvinyl alcohol or sorbitan esters. Both types of lipid nanoparticles may be prepared by a procedure including high pressure homogenization or microemulsion formation.

The pharmaceutical composition of the invention may conveniently be in the form of a composition suitable for topical, in particular dermal, application, such as a gel, lotion, cream or other type of liquid or semiliquid composition. The composition may, in addition to the conjugate described above, contain one or more pharmaceutically acceptable excipients. Such excipients may include diluents, buffers, surface-active agents, emulsifiers, thickeners, preservatives, and the like. In particular, the composition may include a divalent metal salt such as a calcium, zinc or magnesium salt such as magnesium chloride, as $Mg^{2+}$ ions have been found to enhance the uptake of the carrier particles conjugated to the present cyclic peptides in cells expressing the integrin receptor such as the integrin α2β1 receptor.

The therapeutically active drug included in the carrier particles may conveniently be selected from a vitamin D analogue, such as calcipotriol, calcitriol, maxacalcitol or tacalcitol, a corticosteroid, such as betamethasone or a betamethasone ester, e.g. the valerate or dipropionate, clobetasol or a clobetasol ester, e.g. the propionate, hydrocortisone or a hydrocortisone ester, e.g. the acetate or valerate, a calcineurin inhibitor, such as tacrolimus or pimecrolimus, a PDE4 inhibitor, a p38 MAP kinase inhibitor, a JAK inhibitor, a histamine receptor antagonist, ingenol-3-angelate or a naturally occurring or synthetic nucleotide such as siRNA, miRNA, LNA, PNA, depending on the condition to be treated with the conjugate/composition of the invention. The dose of the drug may vary between wide limits, depending on the type of drug and the type and severity of the condition to be treated, ranging from a few micrograms per gram if the drug is a vitamin D analogue to 0.5-500 mg per g amounts for other drugs such as corticosteroids.

The composition of the invention is intended for topically application in the treatment of dermal diseases or conditions, e.g. a skin inflammatory disease or disorder such as psoriasis, atopic dermatitis, eczema, urticaria, acne, allergic contact dermatitis, irritant dermatitis, a skin barrier deficiency disorder such as Netherton's syndrome, wounds, warts, actinic keratosis or skin cancer, e.g. basal cell carcinoma or squamous cell carcinoma.

EXAMPLES

Example 1

Peptide Synthesis

The head-to-tail cyclized peptides were synthesised with an N-succinimidyl-S-acetyl thiolacetate (SATA) linker by JPT Peptide Technologies GmbH (Berlin, Germany) according to the manufacturer's regular procedures using solid phase synthesis with Fmoc protected amino acids. The head-to-tail cyclized targeting peptide had the sequence H-KHD-NAQS-(SATA)KSTRK-OH (SEQ ID NO: 4)(denoted RKK12) and the control peptide H-KHDNRQS-(SATA)KSTAK-OH (SEQ ID NO: 5)(denoted AKK12). Both peptides contained a Lys(SATA) group used for subsequent conjugation to the terminal PEG chains on the surface of the liposomes (R. J. Kok et al., Bioconjug. Chem. 13, 2002, pp. 128-135).

Preparation of DiD-Labeled Liposomes

The liposomal formulations were prepared by the thin film method described by Bangham et al. (A. D. Bangham et al., *J. Mol. Biol.* 13, 1965, pp. 238-252). Briefly, DSPC (62 mol %), $PEG_{2000}$-DSPE (2.5 mol %), Mal-$PEG_{2000}$-DSPE (2.5 mol %) and cholesterol (33 mol %) were dissolved in chloroform:methanol (9:1 w/w). A volume of 1 ml DiD (200 µg/ml in ethanol) was added for labelling purposes. The organic solvent was evaporated, and the lipid film was flushed with nitrogen gas for 5 min. The lipid film was hydrated with HBS-E buffer (10 mM HEPES, 136 mM NaCl and 1 mM EDTA, pH=7.4) to a final concentration of 15 mM lipid to form large multilamellar vesicles (LMVs). To obtain small unilamellar vesicles (SUVs), the LMVs were extruded ten times through two stacked 100 nm filters from Whatman (GE Healthcare, Little Chalfont, United Kingdom) using a Liplex extruder from Northern Lipids inc. (Burnaby, BC, Canada), and kept in the dark at 4° C.

Preparation of Calcipotriol Loaded Liposomes

The liposomal formulations loaded with calcipotriol were prepared by the thin film method essentially as described above with following exceptions: The formulation included DSPC (84 mol %), cholate (11 mol %), $PEG_{2000}$-DSPE (2.5 mol %), Mal-$PEG_{2000}$-DSPE (2.5 mol %) and 1 mol % calcipotriol. The lipid film was hydrated at 65° C. with HBS-E for 1 h. The hydrated lipid dispersions contained a final lipid concentration of 8.5 mM and a calcipotriol concentration of 50 µg/ml (0.121 mM). The LMVs were extruded twice through two stacked 200 nm filters (Whatman), followed by eight extrusions through two 100 nm filters.

Peptide Conjugation of Liposomes

The conjugation of peptides to the maleimide groups on the terminal PEG chains on the liposomal outer surface was carried out as described previously (R. M. Schiffelers et al., *J. Control. Release* 91, 2003, pp. 115-122). The cyclic acetyl-protected SATA-peptides were deacetylated in an aqueous solution of 0.5 M HEPES, 0.5 M hydroxylamine-HCl and 25 mM EDTA (pH 7.0) for 30 min at room temperature. The liposomes were incubated with the activated SATA-peptide on a roller bench overnight at 4° C. Liposomes were separated from non-conjugated peptide by ultracentrifugation. Liposomes labelled with DiD were diluted 1:9 with HBS buffer (10 mM HEPES and 136 mM NaCl, pH=7.4) and pelleted by centrifugation at 60,000 rpm for 1 h at 4° C. (Beckman LE-80K Ultracentrifuge fixed angle roter Type 70.1 Ti). The pellet was resuspended in 10 ml HBS buffer and recentrifugated. The liposomes were resuspended in HBS buffer, without EDTA to avoid depletion of $Mg^{2+}$ ions in subsequently experiments, since the presence of $Mg^{2+}$ ions are important for the interaction between the RKKH-binding site and the integrin receptor. Liposomes with calcipotriol were diluted 1:3 with tris buffer (13 mM tris, pH=8.5) and precipitated by centrifugation at 50.000 rpm for 1 h at 4° C. (Beckman L-80 XP-ULTRA fixed angle rotor type 50.2 Ti). The pellet was resuspended in 25 ml tris buffer, recentrifugated. The tris buffer was used for calcipotriol containing liposomes, since calcipotriol is less stable at the lower pH provided by the HEPES buffer. Finally, all liposomal dispersions were diluted to a final lipid concentration of 15 mM and stored in the dark at 4° C. The unconjugated peptides were detected by ultra performance liquid chromatography (UPLC) using the BEH300 C18 column, 1.7 µm, 2.1 mm×500 mm from Waters (Milford, Mass., USA). The eluent gradient was set from 100% of acetonitrile:water:trifluoroacetic acid (5:95:0.1, v/v) to acetonitrile:trifluoroacetic acid (100:0.1, v/v) over 12 min. The peptides were detected by absorbance at 210 nm, and the amount of conjugated peptides was calculated as the total amount of peptides minus the amount of uncoupled peptides.

Characterization of Liposomes

The final concentration of calcipotriol in the liposomal formulations was quantified by high pressure liquid chromatography (HPLC) using a Sunfire C18, 3.5 µm, 150×4.6 mm column (Waters) with acetonitrile:water (60:40, v/v) as the mobile phase. The detection was performed at 264 nm. The final lipid concentrations of liposomes with DiD were assessed by the Rouser determination method (G. Rouser et al., *Lipids* 5, 1970, pp. 494-496). Briefly, approximately 50 nmol of phospholipid was heated to 180° C. After complete evaporation of liquid, 300 µl perchloric acid was added, and a matebles was put on top to avoid evaporation. The samples were incubated at 180° C. for 45 min, cooled to room temperature, and 1 ml water, 0.5 ml molybdate and 0.5 ml freshly prepared 5% ascorbic acid was added. The samples were incubated in a 100° C. water bath for 5 min, cooled to room temperature, and the absorbance was measured at 797 nm. The lipid concentrations for the calcipotriol containing liposomes were assessed using the colorimetric Phospholipids B enzymatic assay from MTI-Diagnostics Gmbh, (Idstein, Germany) as previously described (H. Grohganz et al., *AAPS; Pharm. Sci. Tech.* 4, 2003, E63). Brief, the liposomal dispersions were diluted 1:40, 2.5% Triton $X_{100}$ was added, and the samples were heated above the $T_m$ for 20 min. A volume of 45 µL of all samples was transferred to a microtiter plate, 180 µl of the coloring reagent solution was added, and the plates were incubated at 37° C. After 1 h, the absorbance at 490 nm was measured using a VICTOR™ X3 Multilabel Plate Reader from Perkin Elmer (Waltham, Mass., USA).

The average particle size distribution and polydispersity index (PDI) were determined by dynamic light scattering using the photon correlation spectroscopy technique on samples diluted 1:40 in HBS or tris buffer. The surface charge of the particles was estimated by analysis of the zeta-potential (Laser-Doppler Electrophoresis), on samples diluted 1:40 in water. The measurements were repeated three times per sample (n=1). Both types of measurements were performed at 25° C. using a Zetasizer Nano ZS (Malvern Instruments, Worcestershire, UK) equipped with a 633 nm laser and 173° detection optics. For viscosity and refractive index the values of pure water were used. Malvern DTS v.5.10 software was used for data acquisition and analysis.

Example 2

Cellular Uptake of the Peptide-Conjugated Liposomes

Human epidermal carcinoma cells A431 were subcultured in Dulbecco's modified Eagle's medium (DMEM) containing 3.7 g/l sodium bicarbonate and 4.5 g/l glucose, supplemented with antimicrobial agents, 2 mM L-glutamine and 7.5% (v/v) fetal bovine serum, at 37° C. in a humidified atmosphere containing 5% $CO_2$. Nearly confluent mono-layers of A431 cells were washed with PBS and cells were detached using 1 mM tris-EDTA in PBS. The cells were subsequently suspended in cold PBS supplemented with 1.26 mM $CaCl_2$ and 0.81 mM $MgSO_4$ at 4° C. The cells were counted after centrifugation and $10^5$ cells in 100 µl media were incubated with 100 µl liposomes diluted in PBS supplemented with 1.26 mM CaCl and 0.81 mM MgSO$_4$, different concentrations of DiD-labeled liposomes (10-200 nmol total lipid), RKK12-conjugated liposomes (RKK12-liposomes) or AKK12-coupled liposomes (AKK12-liposomes) for 1 h at 4° C.

Figure 3:
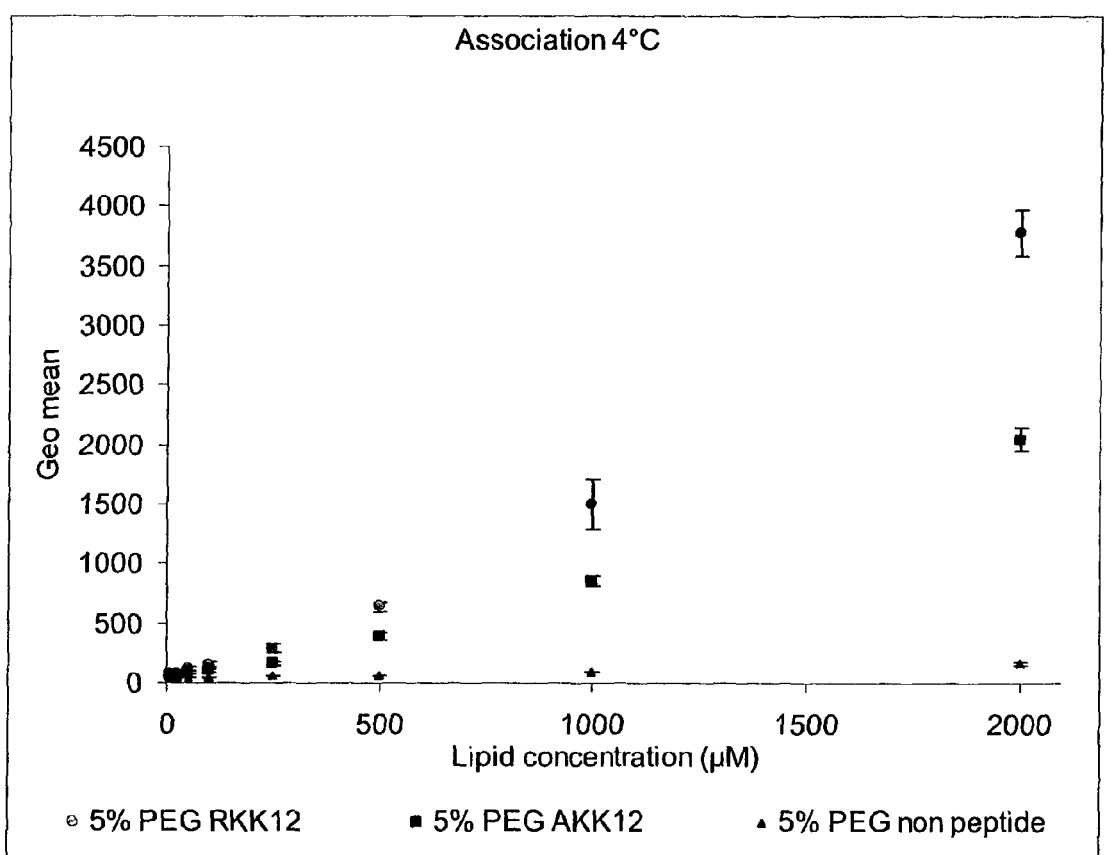
FIG. 3 is a graph showing fluorescence in A431 cells upon incubation at 4° C. with fluorescence labeled liposomes (using the fluorescent dye 1,1'-dioctadecyl-3,3,3',3'-tetramethylindodicarbocyanineperchlorate, DiD) conjugated with either a peptide of the invention ("RKK12") or a control peptide ("AKK12") with low affinity for the integrin $\alpha 2\beta 1$ receptor but a similar charge as the peptide of the invention. The fluorescence measured for cells incubated with liposomes conjugated with a peptide of the invention is much higher than in cells incubated with liposomes conjugated to the control peptide. This suggests a specific binding of the peptide of the invention to the integrin $\alpha 2\beta 1$ receptor. Cells incubated with non-conjugated liposomes did not show any association of the liposomes.
Figure 5:
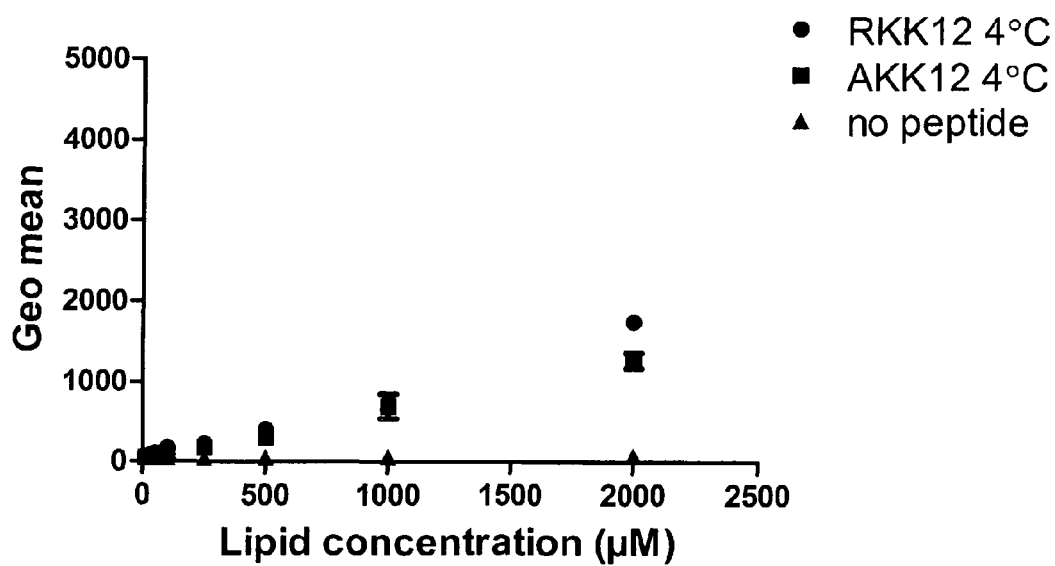
FIG. 5 is a graph showing the cellular binding of fluorescence labeled liposomes conjugated with either a peptide of the invention ("RKK12") or a control peptide ("AKK12") with low affinity for the integrin $\alpha 2\beta 1$ receptor after incubation at 4° C. at low $Mg^{2+}$ concentrations. The binding of liposomes conjugated with the peptide of the invention was only slightly higher than the uptake of liposomes conjugated with the control peptide, suggesting that the $Mg^{2+}$ ion concentration is important for the specific interaction of the cells and the peptide of the invention.

The results of this experiment are shown in FIG. 3 from which it appears that cells incubated with RKK12-liposomes are significantly more fluorescent than cells incubated with AKK12-liposomes or non-conjugated liposomes as a result of specific binding of the RKK12 peptide to the integrin α2β1 receptor present on the surface of the A431 cells. It appears from FIG. 5 that at low Mg$^{2+}$ concentrations the association of the RKK12-conjugated liposomes is only slightly higher than that of the AKK12-conjugated liposomes. This suggests that the Mg$^{2+}$ ion concentration is important for the specific interaction between the cells and the liposomes conjugated with the RKK12 peptide.

In the cellular internalization of liposomes experiment, similar different concentrations of DiD-labeled liposomes (10-200 nmol total lipid) RKK12-liposomes were incubated for 1 hour at 37° C. In the experiment with low Mg$^{2+}$ concentrations the peptides were diluted in PBS which was not supplied with CaCl$_2$ or MgSO$_4$. At the end of the incubation period, cells were washed three times in the 5% BSA supplemented PBS-buffer at 4° C., and resuspended in 200 µl PBS supplied with 5% BSA after which they were analyzed on a FACScalibur flow cytometer (Becton-Dickinson). Results were analyzed using WinMDI software version 2.8 (Joseph Trotter, USA).

Figure 4:
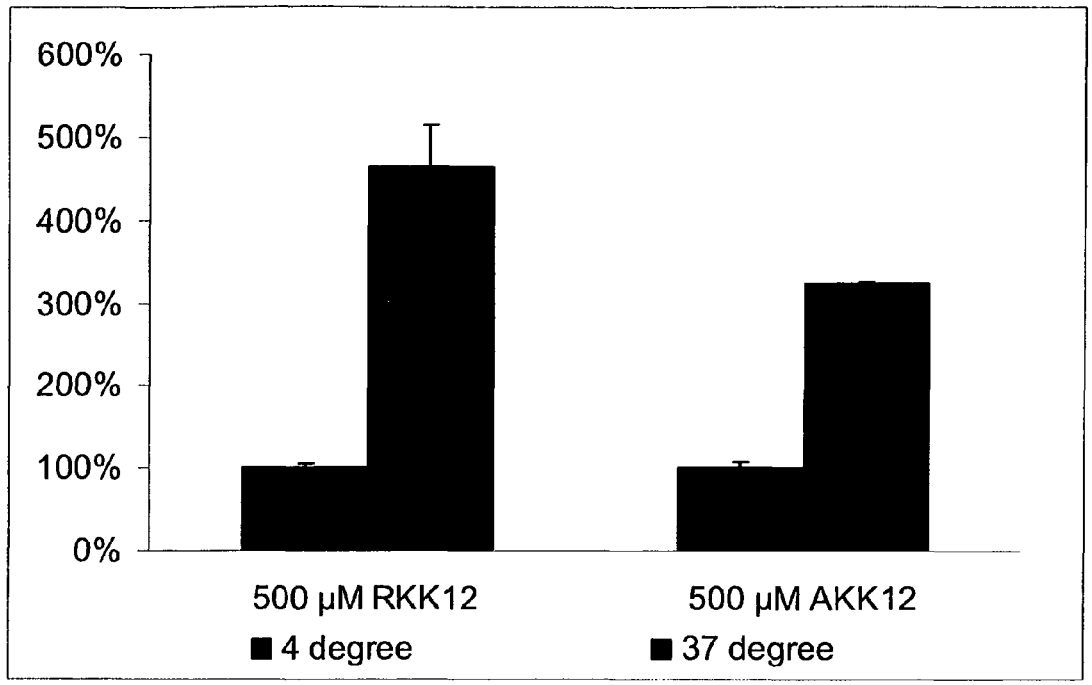
FIG. 4 is a graph showing the cellular uptake of fluorescence labeled liposomes conjugated with either a peptide of the invention ("RKK12") or a control peptide ("AKK12") with less affinity for the integrin $\alpha 2\beta 1$ receptor after incubation at 4° C. or 37° C. Incubation at 37° C. led to a substantial increase in fluorescent cells compared to incubation at 4° C., which is most likely the result of endocytosis taking place at 37° C. Uptake of the liposomes by endocytosis was highest for the liposomes conjugated with the peptide of the invention, suggesting that the uptake is specific and depends on the affinity to the integrin $\alpha 2\beta 1$ receptor.

The results of the internalization experiment are shown in FIG. 4 from which it appears that peptide-conjugated liposomes are internalized by endocytosis at 37° C. However, the internalization is highest for the RKK12-conjugated liposomes, suggesting that the uptake is specific and dependent on the affinity for the integrin α2β1 receptor.

Example 3

Keratinocyte Interaction with Peptide-Conjugated Liposomes Loaded with Calcipotriol Adult human epidermal keratinocytes (HEKa) were obtained from Cascade Biologics (Portland, Oreg., USA) and cultured in EpiLife Medium (Cascade Biologics) containing human keratinocyte growth supplement and gentamicin/Amphotericin B (Cascade Biologics) at 37° C. in a humidified atmosphere with 5% CO$_2$. For the cell interaction assay, 2×10$^5$ exponentially growing keratinocytes were seeded one day prior to treatment. On the following day (at 80% confluency), the medium was renewed, and the cell culture media was supplied with 15 µl of liposome suspension for a final concentration of 10$^{-7}$ M calcipotriol in the well, 15 µl placebo liposomal suspension, or calcipotriol in 0.1% DMSO solution for a final concentration of 10$^{-7}$ M and incubated 1 h at 37° C. The liposomes were conjugated with either the RKK12-peptide or the AKK12-peptide. After 1 h, the cells were washed three times with PBS supplemented with 1% BSA, and 1.5 ml media was added followed by incubation for 24 h at 37° C. Subsequently, the medium was removed, and mRNA was extracted using the RNeasy kit from Quiagen (Hilden, Germany). An amount of 80 ng RNA was translated into cDNA using the High-Capacity cDNA Reverse Transcription kit from Applied Biosystems (Foster City, Calif., USA). For qPCR, cDNA was amplified in triplicate according to manufacturer's protocol (Applied Biosystems, cathelicidin antimicrobial peptide (CAMP) Hs00189038_m1 and GAPDH Hs99999905_m1). The expression level of CAMP was normalized to the expression level of the housekeeping gene Glyceraldehyde-3-phosphate dehydrogenase (GAPDH). The relative change in the expression of CAMP was quantified using the comparative C$_T$ method ($2^{-\Delta\Delta Ct}$)(K. J. Livak and T. D. Schmittgen, *Methods* 25, 2001, pp. 402-408).

Figure 6:
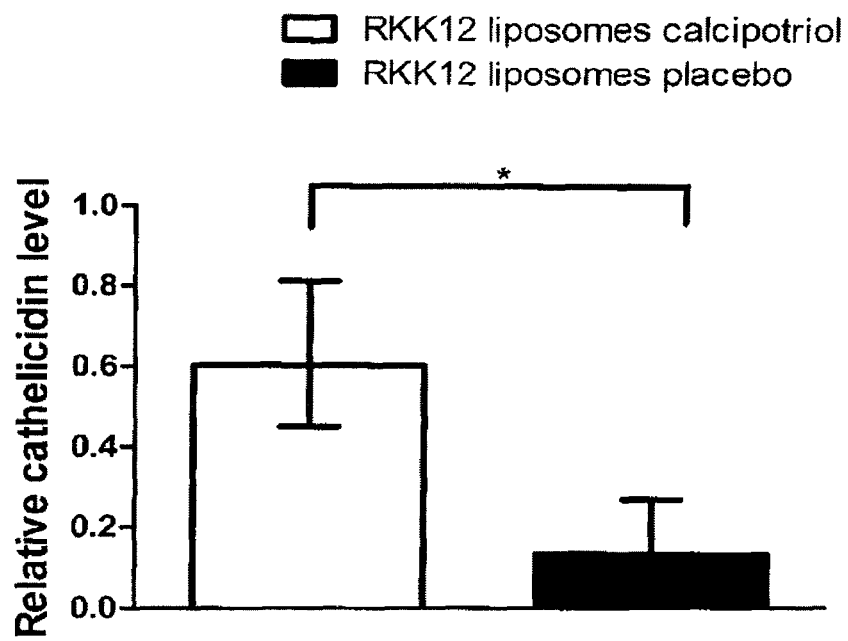
FIG. 6 is a graph showing the biological effect of RKK12-conjugated liposomes loaded with calcipotriol in keratinocytes. The levels of cathelicidin were detected by qPCR and normalized to the level of GAPDH. The relative change in the gene expression level was calculated using the comparative Ct method, using 0.1 µM calcipotriol in a DMSO solution as a reference (set to 1). Calcipotriol-loaded RKK12-conjugated liposomes (empty bar), placebo RKK12-conjugated liposomes (grey bars). The level of cathelicidin was significant increased after incubation of RKK12-conjugated liposomes loaded with calcipotriol compared to the level of cathelicidin after incubation with placebo RKK12-conjugated liposomes (p<0.05) indicated by *. Bars denote N calculated from mean ΔCt±SD (n=3).

RKK12-conjugated liposomes loaded with calcipotriol significantly increased the expression of cathelicidin compared to the RKK12-conjugated liposomal placebo formulation (FIG. 6). This confirms that calcipotriol is delivered into the cells and reaches its target site, the vitamin D$_3$ receptor in an active form. Increased levels of cathelicidin have previously been observed upon incubation of HaCat cells with calcipotriol [G. Weber et al., *J. Invest. Dermatol.* 124, 2004, pp. 1080-1082]. AKK12-conjugated liposomes and non-conjugated liposomes were also tested, but there was no significant difference between the formulations (results not shown). The increase in cathelicidin expression verifies that calcipotriol maintains its therapeutic effect upon delivery into the cells when it is formulated in liposomes. The results from confocal images of the fluorescent labelled liposomes suggest that the liposomes are targeted to the cytoplasm of the cells. The Vitamin D3 receptor is located in the cytoplasm as well as in the nucleus of keratinocytes (Barsony et al., 1997). The results suggest that calcipotriol is delivered to the cytoplasm of keratinocyte where it binds to the vitamin D$_3$ receptor before it translocates to the nucleus and induces the transcription of CAMP.

Example 4

Test of Peptide-Conjugated Liposomes Containing Calcipotriol in UV-B Irradiated Integrin α1β2 Transgenic Mice Animals Double transgenic mice expressing the α$_2$β$_1$ integrin receptors under the involucrin promoter were generated on a C57/Bl6 background as described in Carroll et al., supra. The animal study was carried out under similar conditions as described in Teige et al., supra. Animals were bred in an specific pathogen-free (SPF) facility at Taconic Europe, Denmark, and transferred to the SPF facility at LEO Pharma, Ballerup, Denmark. The mice were allowed to acclimatize three weeks prior to the start of the experiment. All mice were between 16 and 30 weeks of age when the experiments were initiated. All animal experiments were approved by the Animal Experiments Inspectorate, Ministry of Justice, Denmark.

Induction of Skin Inflammation

On day 0, the mice in age- and sex-matched groups were anesthetized using 100 mg/kg ketalar, shaved on their back and irradiated with UV-B 2 J/cm. Thereafter mice were dosed with 0.05 mg/kg Temgesic to relieve any pain. Throughout the experiment, the mice were monitored. None of the animals lost 20% or more of their initial weight and no mice developed larger wounds. Consequently, no mice were euthanized prematurely. The recovery from UV-B irradiation was evaluated daily with respect to erythema and scaling in the irradiated area.

Termination and Evaluation

At day 7, the mice were anesthetized using isoflouran and two 8 mm biopsies were taken from the irradiated area. One biopsy was fixed in 4% formalin, dehydrated, embedded in paraffin, randomly sectioned at 3 µm and stained with Masson's Trichrome to clearly separate dermal from epidermal tissue. The histological sections were evaluated by microscopy and pictures were taken of each section at 4× magnification using an Olympus DP71 camera connected to a Nikon ECLIPSE E400 microscope. The mean epidermal thickness was calculated as the epidermal area divided by the epidermal surface length using the program Visiopharm Integrator System (VIS) (Visiopharm, Hørsholm, Denmark). The other biopsy was snap frozen in liquid $N_2$ and used for analysis of cytokine expression.

Cytokine Analysis

Biopsies were homogenized in 300 µl cell lysis buffer from Cell Signaling Technology Inc. (Danvers, Mass., USA) with protease inhibitor using a Precellys® tissue homogenizer with Cryolys cooling (Bertin Technologies, Montigny-le-Bretonneux, France). The samples were left on ice for 30 min, and the lysate was cleared by centrifugation at 15,000×g for 15 min. The protein concentration was determined using the BCA Protein Assay kit (Pierce Biotechnology, Rockford, Ill., US) according to the manufacturer's protocol. The lysate was stored at −80° C. Specific levels of interferon gamma (IFN-γ), IL-1β, IL-2, IL-4, IL-5, keratinocyte-derived chemokine (KC) (homolog to human IL-8), IL-10, IL-12 and tumor necrosis factor alpha (TNF-α) were determined with the MULTI-SPOT assay system mouse TH1/TH2 9-plex assay (Meso scale discovery, Gaithersburg, Md., US), according to the manufacturer's protocol.

Test of Formulations in Mice

Liposomal formulations were prepared with 50 µg/ml calcipotriol and characterized as described in Example 1. Different ligands for targeting to the integrin $\alpha_2\beta_1$ receptor were conjugated to the liposomal surface, all formulations contained 84 mol % DSPC 5 mol % PEG-DSPC and 11 mol % cholate. The final formulations were all liposomal suspensions in 13 mM tris, pH=8.5, with a calcipotriol concentration of 50 µg/ml. A volume of 20 µl of the formulations was applied two times daily for 7 days, starting at day 1, 18 hours after the UV-B irradiation.

Statistics

All data are given as means±SD (8-9 mice in each group). The statistical significance of the results was evaluated in excel using the t-test comparing two variations assuming equal variation (p<0.05 was considered significant).

Integrin $\alpha_2\beta_1$ Transgenic Mice have Changed Wound Healing Upon UV-8 Irradiation The healing from the UV-B irradiation was evaluated macroscopically, by daily scoring for erythema and scaling (0—none, 1—slightly, 2—moderate, 3—marked, 4—very marked). The wt mice recovered from the UV-B irradiation by developing a blister, which is reflected by the peak in scaling at day 4. The blister burst after approximately 5-6 days and a pronounced erythema occurred afterwards. The integrin $\alpha_2\beta_1$ transgenic mice showed a faster increase in erythema with scaling, and none of the transgenic mice developed a blister. On day 7, the integrin $\alpha_2\beta_1$ transgenic mice had formed a thickened scalp-like lesion with demarcated erythema resembling a clinical psoriasis-like phenotype. No similar lesions occurred in the wt mice, where lesions with more even erythema and no scalp were observed. The macroscopic evaluation of the integrin $\alpha_2\beta_1$ transgenic mice fits well with the transgenic mice as a model for psoriasis.

Altered Level of Inflammatory Cytokines in the Integrin $\alpha_2\beta_1$ Transgenic Mice Cytokine levels in the skin were evaluated, and significantly increased levels of the pro-inflammatory cytokines IL-1β, IL-12, KC and TNF-α were observed in irradiated mice compared to non-irradiated mice. The levels of IL-1β and KC were significantly decreased in the UV-B irradiated integrin $\alpha_2\beta_1$ transgenic mice compared to the levels in the UV-B irradiated wt mice (t-test, p<0.05). A tendency of decreased IL-10 was also observed, but the difference between integrin $\alpha_2\beta_1$ transgenic mice and wt was not significant (t-test, p=0.1). Previously, reduced levels of IL-10 have been suggested to distinguish psoriasis from regular wound healing (B. J. Nickoloff et al., *J. Investig. Dermatol. Symp. Proc.* 11(1), 2006, pp. 16-29). Overall, the reduced cytokine levels confirmed an altered immune response to UV-B irradiation in the integrin $\alpha_2\beta_1$ transgenic mice compared to wt mice, but it is not certain if it resembles the unbalanced cytokine levels in human plaque psoriasis.

Figure 7:
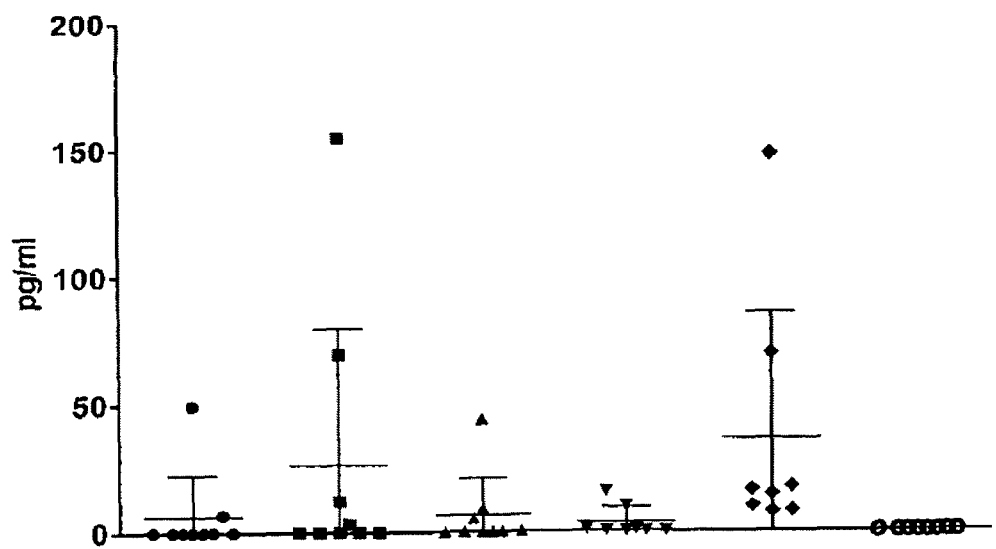
FIG. 7 is a graph showing IL-10 levels in skin biopsies from integrin $\alpha_2\beta_1$ transgenic mice treated with calcipotriol in different liposomal formulations. The results for each mice are displayed ●—UV-B irradiated Integrin $\alpha_2\beta_1$ transgenic mice, ■—Integrin $\alpha_2\beta_1$ transgenic mice treated with RKK12-peptide conjugated liposomes loaded with calcipotriol, ▲—UV-B irradiated integrin $\alpha_2\beta_1$ transgenic mice treated with AKK12-peptide conjugated liposomes loaded with calcipotriol, ▼—UV-B irradiated integrin $\alpha_2\beta_1$ transgenic mice treated with placebo RKK12-peptide conjugated liposomes, ◆—UV-B irradiated wt mice, ○—non-treated wt mice. Lines denote mean±SD (n=8).

Test of Calcipotriol Formulations in UV-8 Irradiated Integrin $\alpha_2\beta_1$ Transgenic Mice Different calcipotriol containing liposomal formulations were tested in the integrin $\alpha_2\beta_1$ transgenic mice. While no statistically significant difference was observed between the treated and non-treated integrin $\alpha_2\beta_1$ transgenic mice, there is a tendency that treatment with calcipotriol affects the level of IL-10 (FIG. 7). An increased level of IL-10 was detected in the biopsies from the UV-B irradiated mice treated with RKK12-peptide conjugated liposomes loaded with calcipotriol compared to the level of IL-10 detected in the biopsies from the non-treated mice, mice treated with placebo RKK12-peptide conjugated liposomes or mice treated with the AKK12-peptide conjugated liposomes loaded with calcipotriol.

In humans, the level of IL-10 is decreased during psoriasis compared to regular wound healing. This effect was also observed in the transgenic mice, where the level of IL-10 decreased in the psoriasis-like lesions on the transgenic mice, compared to the level of IL-10 in in the lesions of wild type (wt) mice (FIG. 7). When human psoriasis patients are treated with calcipotriol, the levels of IL-10 in the lesions is increased. The murine level of IL-10 in the skin after treatment of the transgenic mice with calcipotriol-loaded liposomes suggests that the application of the calcipotriol-loaded RKK12-conjugated liposomes may have a similar effect. It suggests that the receptor-targeted liposomes may increase the efficacy of calcipotriol in the treatment of psoriasis. This confirms the results seen in Example 2 where the conjugation of the RKK-12 peptide to the surface of liposomes was found to increase association and internalisation of liposomes to cells expressing the human integrin $\alpha_2\beta_1$ receptor. It should be noted, however, that the differences in IL-10 levels in the treated and untreated mice are not statistically significant since the experimental standard deviations are very high, but there is a tendency that the targeting ligand has an effect in vivo.

The invention claimed is:

1. A pharmaceutical composition for topical application comprising a conjugate of a drug-containing carrier particle and a cyclic peptide capable of binding specifically to the α2 I domain of the integrin α2β1 receptor of the subgroup of collagen binding integrin receptors, said peptide having the amino acid sequence (SEQ ID NO: 2)
Ser-Thr-Arg-Lys-Lys-His-Asp-Asn-Ala-Gln-Ser-Lys-L wherein
L is a linker moiety comprising a thiol group that is suitable for conjugating the drug-containing carrier particle; and
a pharmaceutically acceptable carrier or excipient.

2. A composition according to claim 1, wherein L is synthesized from S-succinimidyl-S-thioacetate (SATA), N-hydroxysuccinimidyl 3-(2-pyridyldithio) propionate (SPDP), SATP, or SAT-PEO4-Ac.

3. A composition according to claim 1 wherein the cyclic peptide is capable of binding specifically to the α2 I domain of the integrin α2β1 receptor.

4. A composition according to claim 1, wherein the drug-containing carrier particle is a liposome, a niosome, a transfersome, a polymeric nanoparticle or a lipid nanoparticle.

5. A composition according to claim 4, wherein the liposome comprises one or more of the lipids dipalmitoylphosphatidylcholine, disteraroylphosphatidylethanolamine, distearoylphosphatidylcholine, disteraroylphosphatidylglycerol, dioleoylphosphatidylethanolamine, dimyristoylphosphatidylcholine, dimyristoylphosphatidylglycerol, sphingomyelin, soy phosphatidylcholine, egg phosphatidylcholine, cholesterol or cholate.

6. A composition according to claim 5, wherein at least one lipid included in the liposomes comprises PEG groups attached thereto.

7. A composition according to claim 4, wherein the polymeric nanoparticle comprises one or more of polylactic acid, polyglycolic acid, poly(lactide-co-glycolide), poly(ϵ-caprolactone), polyvinylalcohol, poly(methyl methacrylate), polydimethylsiloxane or chitosan.

8. A composition according to claim 4, wherein the drug included in the carrier particle is a vitamin D analogue, a corticosteroid, a calcineurin inhibitor, a PDE4 inhibitor, a p38 MAP kinase inhibitor, a JAK inhibitor, a histamine receptor antagonist, ingenol-3-angelate, or a naturally occurring or synthetic nucleotide such as siRNA, miRNA, LNA or PNA.

9. A composition according to claim 8, wherein the vitamin D analogue is calcipotriol.

10. A composition according to claim 1 for targeting a therapeutic drug to a keratinocyte expressing on its surface the integrin α2β1 receptor of the subgroup of collagen binding integrin receptors.

11. A method of treating a dermal inflammatory disease or condition, the method comprising administering to a patient in need thereof an effective dose of a composition according to claim 8.

12. The method of claim 11, wherein the dermal inflammatory disease or condition is selected from the group consisting of psoriasis, atopic dermatitis, eczema, urticaria, acne, allergic contact dermatitis and irritant dermatitis.

\* \* \* \* \*

SEQUENCE LISTING

<160> NUMBER OF SEQ ID NOS: 5

<210> SEQ ID NO 1
<211> LENGTH: 12
<212> TYPE: PRT
<213> ORGANISM: Artificial Sequence

```
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be Ser, Thr, Leu or Ile
<220> FEATURE:
<221> NAME/KEY: misc_feature
<222> LOCATION: (2)..(2)
<223> OTHER INFORMATION: Xaa can be Thr or Ser
<220> FEATURE:
<221> NAME/KEY: misc_feature
<222> LOCATION: (3)..(3)
<223> OTHER INFORMATION: Xaa can be Arg
<220> FEATURE:
<221> NAME/KEY: misc_feature
<222> LOCATION: (4)..(5)
<223> OTHER INFORMATION: Xaa can be Lys
<220> FEATURE:
<221> NAME/KEY: misc_feature
<222> LOCATION: (6)..(6)
<223> OTHER INFORMATION: Xaa can be His or Lys
<220> FEATURE:
<221> NAME/KEY: misc_feature
<222> LOCATION: (7)..(7)
<223> OTHER INFORMATION: Xaa can be Asp, Glu, Ala, Asn or Gln
<220> FEATURE:
<221> NAME/KEY: misc_feature
<222> LOCATION: (8)..(8)
<223> OTHER INFORMATION: Xaa can be Gln, Asn, Ala, Glu or Asp
<220> FEATURE:
<221> NAME/KEY: misc_feature
<222> LOCATION: (9)..(9)
<223> OTHER INFORMATION: Xaa can be Ala, Gly, Val, Leu or Ile
<220> FEATURE:
<221> NAME/KEY: misc_feature
<222> LOCATION: (10)..(10)
<223> OTHER INFORMATION: Xaa can be Gln, Asn, Glu or Asp
<220> FEATURE:
<221> NAME/KEY: misc_feature
<222> LOCATION: (11)..(11)
<223> OTHER INFORMATION: Xaa can be Ser or Thr
<220> FEATURE:
<221> NAME/KEY: MOD_RES
<222> LOCATION: (12)..(12)
<223> OTHER INFORMATION: Linker moiety on 3' end - suitable for
      conjugating a drug-containing carrier particle, the linker moiety
      comprising a thiol group; and a pharmaceutically acceptable
      carrier or excipient

<400> SEQUENCE: 1

Xaa Xaa Xaa Xaa Xaa Xaa Xaa Xaa Xaa Xaa Xaa Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: Linker moiety on 3' end - suitable for
      conjugating a drug-containing carrier particle

<400> SEQUENCE: 2

Ser Thr Arg Lys Lys His Asp Asn Ala Gln Ser Lys
1               5                   10

<210> SEQ ID NO 3
<211> LENGTH: 11
<212> TYPE: PRT
<213> ORGANISM: Artificial Sequence
<220> FEATURE:
```

```
<223> OTHER INFORMATION: Synthetic peptide

<400> SEQUENCE: 3

Cys Thr Arg Lys Lys His Asp Asn Ala Gln Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Location of N-succinimidyl-S-acetyl
      thiolacetate (SATA) linker

<400> SEQUENCE: 4

Lys His Asp Asn Ala Gln Ser Lys Ser Thr Arg Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: location of N-succinimidyl-S-acetyl
      thiolacetate (SATA) linker

<400> SEQUENCE: 5

Lys His Asp Asn Arg Gln Ser Lys Ser Thr Ala Lys
1               5                   10
```